United States Patent

Matsunaga et al.

[11] Patent Number: 6,118,280
[45] Date of Patent: Sep. 12, 2000

[54] METHOD FOR DETECTING DEFECTS IN DIELECTRIC FILM

[75] Inventors: Hideki Matsunaga, Kanagawa; Isao Suzuki, Chiba; Hiroshi Tomita, Kanagawa; Shiro Takeno, Kanagawa; Akira Okada, Kanagawa, all of Japan

[73] Assignee: Kabushiki Kaisha Toshiba, Kanagawa-ken, Japan

[21] Appl. No.: 09/049,201

[22] Filed: Mar. 27, 1998

[30] Foreign Application Priority Data

Mar. 31, 1997 [JP] Japan .................. P09-079864

[51] Int. Cl.$^7$ .................................................. G01N 27/00
[52] U.S. Cl. .................. 324/557; 324/765; 204/434; 205/791.5
[58] Field of Search ........................ 324/425, 551, 324/557, 765, 769; 205/791.5, 170, 182; 204/434

[56] References Cited

U.S. PATENT DOCUMENTS 3,379,625   4/1968   Csabi ............................ 205/791.5
5,015,346   5/1991   Guilinger ....................... 205/791.5

OTHER PUBLICATIONS

W. J. Shannon, "A Study of Dielectric Defect Detection by Decoration With Copper" RCA Review, vol. 31, Jun. 1970, pp. 431–438.

Manabu Itsumi et al., "The origin of defects in SiO$_2$ thermally grown on Czochralski silicon substrates" J. Appl. Phys., vol. 78, No. 3, Aug. 1995, pp. 1940–1943.

Primary Examiner—Josie Ballato
Assistant Examiner—T. R. Sundaram
Attorney, Agent, or Firm—Finnegan, Henderson, Farabow, Garrett & Dunner, L.L.P.

[57] ABSTRACT

Disclosed are a method and an apparatus for detecting a defect in a dielectric film. The dielectric film is electrified in an electrolyte solution containing a metal in such a manner the dielectric film is charged negative, thereby the metal is deposited on the dielectric film at a position corresponding to the defect. The detecting method has a first deposition step for forming a first metal deposit on the dielectric film in an annular form surrounding the position corresponding to the defect; and a second deposition step for forming a second metal deposit located on the position corresponding to the defect, on the dielectric film. The detecting apparatus has a vessel for accommodating the electrolyte solution; a first electrode for electrifying the dielectric film and a second electrode; and an electric power source for controllably applying a voltage to electrifying between the first electrode and the second electrode in which a value and a direction of the applied voltage is variable.

10 Claims, 2 Drawing Sheets

METHOD FOR DETECTING DEFECTS IN DIELECTRIC FILM

BACKGROUND OF THE INVENTION

1. Field of the Invention

The present invention relates to a method and apparatus for detecting defects in dielectric films. Particularly, the present invention relates to method and apparatus for detecting and measuring detects in a dielectric film which is provided on the surface of silicon substrate.

2. Related Art

There are a number of means which have conventionally proposed, based on various principles, to detect defects in dielectric film which is provided on the surface of a silicon substrate. Example of such means include (1) electrical methods using capacitors, (2) methods using chemical selective etching, (3) electrochemical methods such as bubble generation etc., (4) chemical methods such as Nomarski method, (5) microprobe analysis methods using X-rays or electron beams, and (6) profile observation by a mechanical probe, as reviewed in RCA Review, Vol. 34, pp. 656–690 (1973) and Solid State Technology, Vol. 17, pp. 35–42 (1974).

However, for evaluation of films ($SiO_2$, SiN, SiON etc.) used in insulating semiconductor elements and gate oxide films in MOS transistors, methods capable of detecting defects under the application of electric field are preferable for the object of the films.

A first method meeting the above requirement includes, for example, a method of measuring the electrical characteristics of MOS capacitors having a structure "metal (M)—oxide film (O)—semiconductor (S)", such as in the above method (1). In this method, the electrical characteristics of the dielectric film is directly measured to determine the presence or absence of defects and is thus a method of evaluating defects with extremely high reliability. However, construction of such MOS capacitors needs various steps requiring vacuum such as sputtering, vapor deposition and low-pressure CVD and steps including photographic etching step etc. Accordingly, there is the drawback that the rapidness and easiness of evaluation are lost.

To overcome the drawback of the first method, electrochemical methods which are capable of completing evaluation in a few steps are very effective, and various methods have conventionally been proposed to realize it. For example, in RCA Review, Vol. 31, pp. 431–438 (1970), a method of depositing copper on defects in a semiconductor silicon substrate having an dielectric film as a cathode by the phenomenon of electrophoresis, using a copper anode in methyl alcohol as solvent is proposed as a second method for overcoming the drawback of the first method. In this method, however, the specific electric conductance of methyl alcohol at 25° C. is as very low as $3\times10^{-7} \Omega^{-1} cm^{-1}$, and the influence of the voltage drop caused by the resistance of the solution is large, so the surface potential of the semiconductor silicon substrate having the dielectric film as the cathode is difficult to keep uniformly on the surface. Accordingly, uneven copper deposition in the surface occurs easily. Further, because of moisture absorption or evaporation of the solution, there are many problems such as easy changes with time in the liquid composition, poor reproducibility etc.

As a third method of overcoming the drawbacks of the first and second methods, Japanese Patent Appln. Laid-Open Publication No. (JPA) Sho 52-132,682 discloses a method of depositing copper above defects in a silicon semiconductor substrate having dielectric film as the cathode by electrochemical plating reaction, which comprises: immersing, in an electrolyte solution composed of aqueous solution containing strongly acidic salt of copper, an anode constituted of an electrically conductive substance not corrosive by said electrolyte solution and a cathode constituted of the semiconductor silicon substrate having dielectric film which is a material to be measured; and applying a direct current voltage across the anode and the cathode so that the applied direct voltage is smaller than the dielectric breakdown voltage of the dielectric film formed on the surface of the silicon substrate. In this method, the effect of the voltage drop due to the electrolyte solution is small, the surface potential of the silicon substrate can be kept uniform on the surface. Accordingly, the uniformity of copper deposition ability in the surface is good. Further, the electrolyte solution is an aqueous solution, so the change with time in the liquid composition caused by moisture absorption or evaporation is not a large problem.

In this method, the area of the copper deposit is varied depending on the size of the defect in the dielectric film, so the size of the defect in the dielectric film can be evaluated relatively by using the areas of the copper deposits on the surface of the dielectric film. In this case, it is possible to determine the central position of the defect by the central position of the deposited copper. If the area of deposited copper is so large that its diameter reaches 10 microns or more, the relative size and distribution of each individual defect in the film can be visually determined in terms of the relative size and distribution of its corresponding deposited copper on the surface.

However, the accuracy of specifying the central position of the defect is deteriorated with increase in area of deposited copper. Accordingly, if copper is deposited in such a size as to permit visual observation, it is difficult to accurately specify the central position of each individual defect for observing the defect. For processing a sample to be directly observed for its sectional defects, it is essential that the central positions of defects can be specified simultaneously and accurately, so the difficulty in specifying the central position of deposited copper is disadvantageous.

On the other hand, if the diameter of deposited copper is as small as 1 micron or less, particularly 0.1 micron or less, the central position of the defect can be accurately specified, but the visual observation of the relative size and distribution of each individual defect on the surface is difficult.

Further, a natural oxide film (silicon dioxide film) on the back of silicon substrate should be previously provided with ohmic electrode using aluminum or indium, making the procedure cumbersome.

SUMMARY OF THE INVENTION

The object of the present invention is to solve the problems in the conventional art and to provide a method and an apparatus for detecting defects in dielectric film, capable of easily and accurately specifying and observing the relative size, position and distribution of each individual defect in dielectric film formed on a silicon substrate.

In order to achieve the above-mentioned object, a method of detecting a defect in dielectric film by electrifying the dielectric film in an electrolyte solution containing a metal in such a manner the dielectric film is charged negative, thereby the metal is deposited on the dielectric film at a position corresponding to the defect, according to the present invention comprises: a first deposition step for forming a first metal deposit on the dielectric film in an annular form surrounding the position corresponding to the center of the defect; and a second deposition step for forming a second metal deposit located on the position corresponding to the center of the defect, on the dielectric film.

In the above method, the second metal deposit has a dimension which is smaller than an inner bore of the first metal deposit.

The first metal deposit has an outer diameter which is 2 $\mu$m or more, and the second metal deposit has a diameter which is 0.3 $\mu$m or less.

The first deposition step comprises: an electrodepositing step for electrifying the dielectric film such as to charge the dielectric film negative and to form a circular metal deposit having a dimension corresponding to an outer diameter of the first metal deposit; and an eluation step for electrifying the dielectric film such as to charge the dielectric film positive and to elute a central portion of the circular metal deposit on the position corresponding to the center of the defect, the central portion having a dimension which is substantially the same as an inner diameter of the first metal deposit, thereby the circular metal deposit is changed into the annular form of the first metal deposit.

In the above method, the electric charge amount, Ed, which is supplied to the dielectric film by electrification at the electrodepositing step, the electric charge amount, Es, which is supplied to the dielectric film by electrification at the eluation step, and the electric charge amount, Ec, which is supplied to the dielectric film by electrification at the second metal deposition step are in a relationship which is represented by the formula:

$$|Ed|>|Es|>|Ec|.$$

In the detecting method, each of the electric charge amounts, Ed, Es and Ec, are regulated by controlling voltage applied to the dielectric film at each of the electrodepositing step, the eluation step and the second metal deposition step.

In the detecting method, the first metal deposit formed at the first deposition step comprises an N number (N is a natural number) of annular deposits being concentrically formed with each other and having different dimensions respectively.

The first metal deposition step comprises said N number of cycles of operation, wherein the Mth (M=1,2,... N) cycle of operation comprises: an electrodepositing step for electrifying the dielectric film such as to charge the dielectric film negative and to form a Mth circular deposit having a dimension corresponding to an outer diameter of the Mth annular deposit; and an eluation step for electrifying the dielectric film such as to charge the dielectric film positive and to elute a central portion of the Mth circular deposit on the position corresponding to the defect, the central portion having the same dimension as an inner diameter of the Mth annular deposit, thereby the Mth circular deposit is change into the Mth annular deposit.

In the above method, an amount of the electric charge supplied to the dielectric film by electrification at the Mth electrodepositing step is represented by $Ed_M$ (M=1,2,... N), an amount of the electric charge supplied to the dielectric film by electrification at the Nth eluation step is represented by $Es_M$ (M=1,2,... N), and an amount of the electric charge supplied to the dielectric film by electrification at the second metal deposition step is represented by Ec, and wherein the amounts, $Ed_M$, $Es_M$ and Ec, are in a relationship which is represented by the formula:

$$|Ed_1|>|Es_1|>|Ed_2|>|Es_2| \ldots >|Ed_N|>|Es_N|>|Ec|$$

The detecting method further comprises: a changing step for changing the metal composition of the electrolyte solution so that the first deposition step is performed in a electrolyte solution having a first metal composition and the second deposition step is performed in a electrolyte solution having a second metal composition which is different from the first metal composition.

Moreover, an apparatus for detecting a defect in dielectric film, according to the present invention comprises: a vessel for accommodating an electrolyte solution containing a metal; a first electrode for electrifying the dielectric film and a second electrode being opposed to the first electrode, the first electrode and the second electrode being arranged in the electrolyte solution; and an electric power source for controllably applying a voltage to electrifying between the first electrode and the second electrode in which a value and a direction of the applied voltage is variable, wherein the metal in the electrolyte solution is deposited on the dielectric film at a position corresponding to the center of the defect when the dielectric film is charged negative by the electric power source, and the deposited metal on the dielectric film elutes at the position corresponding to the center of the defect when the dielectric film is charged positive by the electric power source.

The detecting apparatus further comprises: a control unit for controlling the electric power source in such a manner that a first metal deposit which has an annular form surrounding the position corresponding to the center of the defect and a second metal deposit located on the position corresponding to the center of the defect are formed on the dielectric film.

The control unit controls the electric power source in such a manner that the dielectric film is charged negative to electrify an amount of electric charge represented by Ed, before the dielectric film is charged positive to electrify an amount of electric charge represented by Es, to form the first metal deposit, and that the dielectric film is charged negative to electrify an amount of electric charge represented by Ec, to form the second metal deposit, wherein Ed, Es and Ec are in a relationship which is represented by the formula: $|Ed|>|Es|>|Ec|$.

The control unit comprises a processing unit for calculating a value of voltage appropriate for supplying electric current of each of amounts of electric charge, Ed, Es and Ec, in a predetermined time period by using the value of the electric current measured by the ammeter, and the control unit regulates the electric power source to apply the calculated value of voltage.

Alternatively, the control unit comprises a processing unit for calculating a time period appropriate for supplying each of amounts of electric charge, Ed, Es and Ec, by using the value of the electric current measured by the ammeter, and the control unit regulates the electric power source to electrify for the calculated time period.

The dielectric film is formed on an electrically conductive or semiconductive substrate, and the first electrode has an uneven portion which has sharpness to penetrate natural oxide film on the back of the substrate to make electric connection between the first electrode and the electrically conductive or semiconductive substrate.

The detecting apparatus further comprises: an additive supplier for adding a metal solution to the electrolyte solution to change the metal composition of the electrolyte solution received in the vessel; and an addition controller for controlling addition of the metal solution by the additive supplier so that the first metal deposit and the second metal deposit have different metal compositions from each other.

The detecting apparatus further comprising: a replacer for replacing the electrolyte solution in the vessel with another electrolyte solution so that the first metal deposit and the second metal deposit have different metal compositions from each other.

BRIEF DESCRIPTION OF THE DRAWINGS

The features and advantages of the method and the appratus for detecting defects in dielectric film according to the present invention over the conventional art will be more clearly understood from the following description of the preferred embodiments of the present invention taken in conjunction with the accompanying drawings in which like reference numerals designate the same or similar elements or sections throughout the figures thereof and in which.

DETAILED DESCRIPTION OF THE PREFERRED EMBODIMENT

Figure 1:
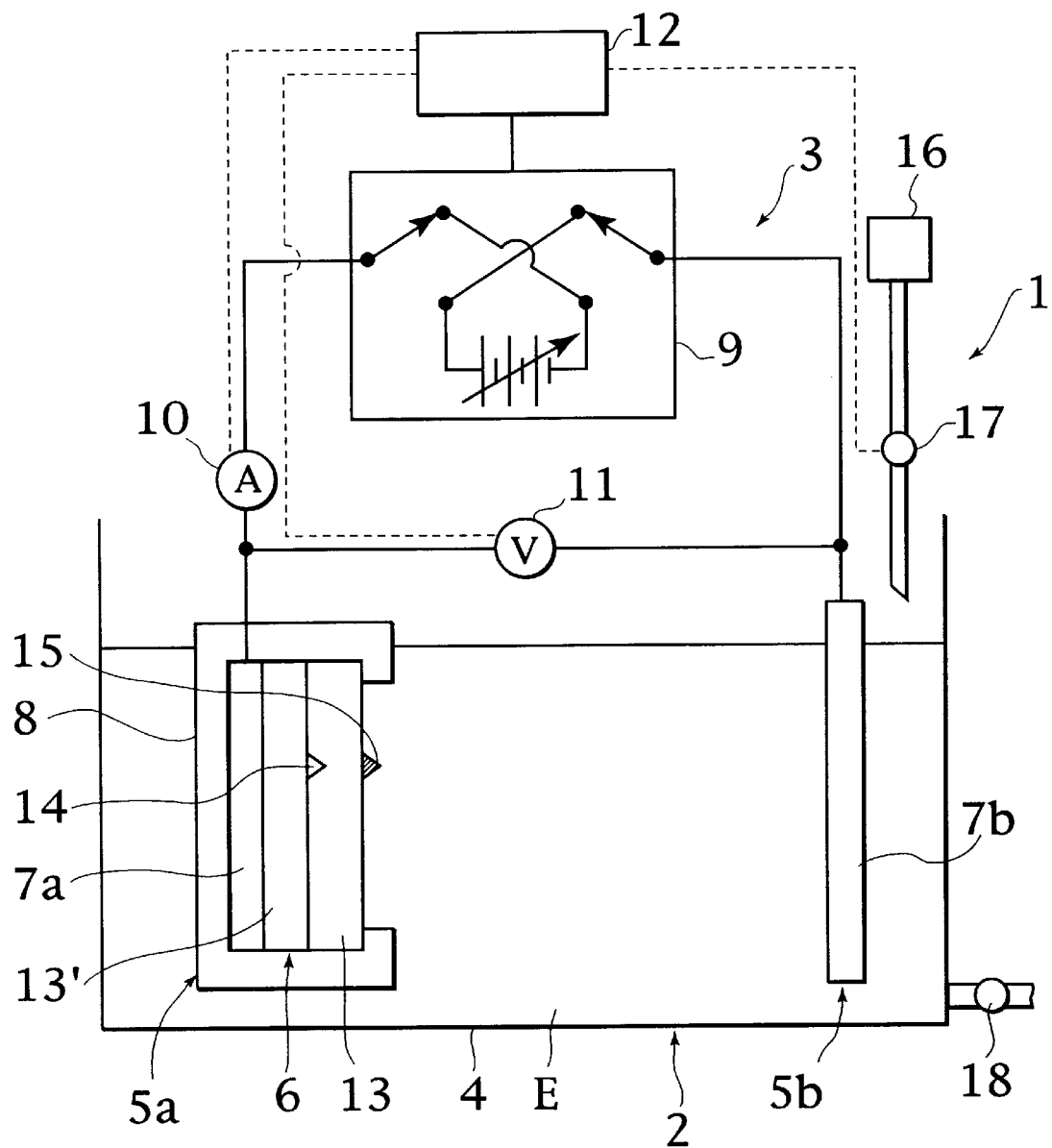
FIG. 1 is a schematic view showing one embodiment of the detection apparatus for carrying out the method of detecting defects in dielectric film according to the present invention.

The present invention is based on a method of detecting defects by applying a voltage to pass an electric current through dielectric film such as nitrides or oxides as a cathode in an electrolyte solution containing metal ions or metal complexes dissolved in water at such a concentration range as not to cause electroless plating or electrochemical concentration depolarization, thereby permitting the metal component in the electrolyte solution to be selectively deposited (electro-deposited) on the surface of the dielectric film, depending on the difference in current values between the position of a defect and the defect-free position in the dielectric film so that the position of the defect in the dielectric film is specified.

The characterizing feature of the present invention resides in forming a annular first metal deposit surrounding the surface position which correspondes to the position of a defect in the dielectric film and a second metal deposit located in said surface position of the defect. The first deposited metal is to show the presence of a defect in the dielectric film and is formed in a size capable of easy detection, and the second deposited metal is to show the central position of the defect accurately and is formed in a smaller size depending on necessary accuracy for specifying the position. In this manner, the role of detecting a defect and the role of specifying its central position are assigned to different metal deposits in order to improve the accuracy and easiness in detecting the defect. Hereinafter, the characterizing features of the present invention are described in detail.

When a voltage such that the dielectric film is on the negative electrode (normal voltage) is applied to pass an electric current, the metal component in the electrolyte solution is initiated to be deposited at the surface position (that is, the position on the surface of the dielectric film just under which a defect is present. In this time, the dielectric film should be just opposite to the electrode to which an anode voltage is applied) corresponding to the position of a defect in the dielectric film, thus forming a circular metal deposit at that position. The rate of depositing the metal is increased with an increase in the applied voltage, and the amount of the deposited metal is expressed as the product of the deposition rate multiplied by the deposition time, so the amount of the deposited metal is in proportion to the value of current flowing with voltage application and the voltage application time. That is, it is in proportion to the amount of the total applied electric charges. If the amount of the deposited metal is increased, the area of the deposited metal (the area of the film surface covered with the deposited metal) is also increased, so if the applied voltage or voltage application time is increased, the area of the deposited metal is also increased. In other words, the area of the metal deposited on the dielectric film can be controlled by regulating the applied voltage and voltage application time.

On the other hand, when a voltage (reverse voltage) is applied so as to permit an electric current (reverse current) to flow in the reverse direction which is opposite to the direction of the electric current (normal electric current) which makes the metal component to deposit on the dielectric film, the elution of the deposited metal is initiated to proceed at the surface position of the defect, thus exposing the dielectric film at that position. As a result, the shape of the deposited metal is changed to a ring surrounding the surface position of the defect. The amount of the eluted metal is in proportion to the electric current flowing by the reverse voltage application and the reverse voltage application time. If the amount of eluted metal is increased, the exposed area (area of the film surface exposed by elution) is also increased, and thus an annular metal deposit of a desired shape can be obtained by suitably regulating the normal voltage, the reverse voltage and the voltage application times.

As can be seen from the above description, the first deposited metal in the present invention is formed by deposition of the metal with the applied normal voltage and then by elution of the deposited metal with the applied reverse voltage as described above. The first deposited metal is an annular metal deposit to indicate that the surface position under which a defect is present is located on the inside thereof. The presence of a larger deposit can be easily recognized, resulting in easy recognition of the defect. Since a size of about 2 $\mu$m or more in diameter, preferably about 10 $\mu$m or more, is required to enable visual recognition, the total electric charges of the normal current for depositing the metal is regulated such that the outer diameter of the first deposited metal meets such a requirement. The inner diameter of the first deposited metal is regulated in such a size as to encompass the second deposited metal. The width of the first deposited metal, that is, the difference between the outer radius and the inner radius is set at such a degree as to enable visual recognition. Preferably, it is set at 0.5 $\mu$m or more.

The first deposited metal is not limited to a single circle and may be formed into a plurality of concentric circles. In this case, the outer diameter of the outermost circle is set to have a size capable of visual recognition and the inner diameter of the innermost circle is set to have a size capable of encompassing the second deposited metal.

After the first deposited metal was formed, the second deposited metal is formed by depositing the metal inside of the first deposited metal by passing a normal electric again. To specify the surface position of the defect, higher accuracy is attained where the size of the deposited metal is smaller, and the size of the second deposited metal is suitably set in consideration of the accuracy required for detecting the defect. In order that the maximum error in specifying the surface position of the defect is about 0.1 $\mu$m or less, the total applied electric charges are determined such that the diameter of the second deposited metal is about 0.3 $\mu$m or less, preferably 0.03 $\mu$m or less.

The first deposited metal and the second deposited metal may be different metals. This can be realized by changing the metal composition of the electrolyte solution for carrying out the deposition procedure, that is, by replacing the electrolyte solution with another solution or by adding another metal component. For example, there is a method in which copper is deposited as the first deposited metal and a noble metal such as platinum is deposited as the second deposited metal.

According to the above description, the first annular deposited metal having a size capable of visual recognition is formed by passing normal current and reverse current, and the second deposited metal which is smaller than the first deposited metal is formed by passing normal current. Although detection of defects in dielectric film can be used effectively in particular in semiconductor samples etc., the size of defects in such semiconductor samples is not at such a level that its position can be specified by visual inspection, and thus the observation of the defect by use of the deposited metal is carried out if necessary by using known observation means such as optical microscope, electron microscope etc. Accordingly, in such a case, the sizes of the first deposited metal and the second deposited metal are suitably set so as to be adapted to the observation means used. In this case too, the effect achieved by constituting concentric circular deposits consisting of the first deposited metal and the second deposited metal is the same as that at the level of visual inspection.

The electrolyte solution for carrying out the above procedures contains the metal component in the form of metal ions or metal complexes. Specifically, a solution of the metal in an acid is used. This electrolyte solution may contain any metal element if it does not prevent the metal directly or indirectly from being deposited on the surface position of a defect in the dielectric film, but the metal component is preferably a metal element with lower ionization tendency than hydrogen to reduce the time required for preparing a sample for detection of defects and to prevent the deposited metal from being dissolved again by washing with water etc. after deposition. For example, copper and noble metals such as gold, silver and platinum can be illustrated. The concentration of the metal component should be in such a range as not to cause electroless plating or electrochemical concentration depolarization. The metal component contained in the electrolyte solution is not limited to one metal but may include a plurality of metals.

If a metal such as copper with low ionization tendency is used, there is a small possibility that a deposit may be formed whether an electric current is applied or not, thus making it difficult to determine whether the deposited metal on the dielectric film has occurred due to the presence of a defect or not. To control such deposition not related to the applied current, there is a method of incorporating a complexing agent for making a complex with a metal component into the electrolyte solution. The complexing agent includes e.g. ammonium ion ($NH_4^+$), cyan ion ($CN^-$), organic acids (oxalic acid, tartaric acid, citric acid, acetic acid, etc.), chelating agents (EDTA, CyDTA, NTA, EDDHA, etc.) and the like. When incorporated into the electrolyte solution containing copper, such complexing agents also have the effect of making fine the deposited particles of copper.

The electrolyte solution can be prepared by suitably dissolving the above metal component in an aqueous solution of an acid such as hydrochloric acid, sulfuric acid, nitric acid etc. However, nitric acid makes the deposited metal easily dissolved again. Accordingly, hydrochloric acid or sulfuric acid is preferably used for accurately controlling the deposition and elution of the metal component. However, sulfuric acid remains easily on the surface of the dielectric film and its rapid removal by washing with water is difficult, so if the electrolyte solution containing sulfuric acid is used, the metal may be easily deposited even on the surface of a defect-free dielectric film. Accordingly, an aqueous solution of hydrochloric acid or an aqueous solution of dilute nitric acid is preferably used.

In dissolving the deposited metal by applying reverse voltage to the dielectric film, any electrolyte solution can be used if only the target metal can be dissolved and removed from the deposited metal and detection of the defect is not prevented directly or indirectly, but an oxidative dilute acid solution is preferably used. In particular, an oxidative dilute acid solution such as a liquid of dilute nitric acid, a mixed solution of hydrogen peroxide and dilute hydrochloric acid, and a mixed solution of dilute nitric acid and dilute hydrochloric acid is preferably used as the electrolyte solution.

Prior to detection of defects is conducted, copper adhering to the surface of the dielectric film can be removed by washing the dielectric film with a solution containing an oxidative acid solution. Accordingly, the metal can be deposited further accurately upon application of direct current voltage to the dielectric film.

The application of voltage to the dielectric film can be effected by contacting the dielectric film with an electrically conductive member to fix them to each other, and applying voltage to the electrically conductive member, so that the voltage is applied uniformly to the whole of the dielectric film. If the dielectric film to be detected for defects is formed on silicon substrate, the back face of the silicon substrate (opposite face to the dielectric film to be evaluated) is contactingly fixed to the electrically conductive member, and cathode voltage is applied to the silicon substrate. In this case, the electrically conductive member is preferably contacted with the whole of the back face of the silicon substrate. The material for forming the electrically conductive member may be any solid electrically conductive at room temperature. For example, copper, aluminum, silver, iron, gold, platinum palladium and the like can be illustrated, among which copper, aluminum, silver and iron are preferable because of their inexpensive prices and excellent processability. Usually, natural oxide film has been formed on the silicon substrate, so the surface of the electrically conductive member to be contacted with the silicon substrate is preferably provided with uneven portion having sharp top which can penetrates through the natural oxide film on the back of the silicon substrate into the inside metallic silicon. Larger uneven portion brings about its higher effect, but too large uneven portion may easily break the electrically conductive member. Too small uneven portion, when overlaid on the silicon substrate, is difficult to penetrate through the natural oxide film on the back of the silicon substrate. In consideration of these, the size of the uneven portion is 0.02 to 200 $\mu$m, preferably 0.1 to 20 $\mu$m. The method for providing the uneven portion on the surface of the electrically conductive member may be any method if it does not prevent a metal having lower ionization tendency directly or indirectly from being deposited on the surface around the center of a defect in the dielectric film, and such uneven portion may be made by scratching the whole surface of the electrically conductive metal thin plate with a pair of metal tweezers with sharp tops, needles etc. By making an electrical connection with the silicon substrate by allowing the sharp uneven portion to penetrate through the natural oxide film on the back of the silicon substrate, the formation of ohmic electrode is unnecessary and the operation is thus made easy.

The means of fixing the dielectric film or the substrate having the dielectric film formed thereon to the electrically conductive member may be any means insofar as a metal with low ionization tendency is not prevented directly or indirectly from being deposited on the surface around the center of a defect in the dielectric film, and the means of sandwiching the ends of the dielectric film or the substrate with two plastic sheets with screws and then fixing it between the sheets by tightening the screw is preferably used. Any means can be used to prevent the electrolyte solution from contacting the back of the dielectric film or of the back of the substrate, insofar as a metal with low ionization tendency is not prevented directly or indirectly from being deposited, and an O-shaped ring made of rubber may be used to insert between the plastic material and the dielectric film or the substrate. The first electrode part having the dielectric film incorporated therein is thus constituted.

The second electrode part to be paired with the first electrode part is constituted of an electrode plate made of a material which is a solid and electrically conductive at room temperature, and any metal having lower ionization tendency than hydrogen can be used. For example, copper, gold, platinum, palladium etc can be illustrated. Noble metals such as gold and platinum are chemically stable and thus preferable. Copper is inexpensive and excellent in processability. If the second electrode part contains the metal component of the electrolyte solution, the same metal component is eluted from the second electrode into the electrolyte solution by electrifying normal current between the first and second electrode parts, so this can be used as a means of supplying the metal component into the electrolyte solution.

The dielectric film having the first and second deposited metals formed thereon is washed with water as necessary for removal of adherent materials other than the deposited metal and then subjected to observation for the deposited metals.

As described above, the means of regulating the direction and level of direct voltage to apply normal voltage and reverse current voltage may be any means insofar as a metal with lower ionization tendency is not prevented directly or indirectly from being deposited on the surface around the center of defects in the dielectric film, and it is possible to use a power source capable of applying normal voltage and reverse voltage alternately to the electrodes and simultaneously capable of arbitrarily changing the level of the normal voltage and the reverse voltage. A power source capable of accurately regulating relatively high to low voltage is preferably used to form the first and second deposited metal accurately in a short time. Such a power source includes a variable direct voltage generator capable of arbitrarily varying the level and the direction of direct current voltage, and a combination of a variable direct current voltage generator capable of arbitrarily varying the level of the direct current voltage and a connecting switch. For easy operation, the variable direct voltage generator capable of arbitrarily varying the direction and level of direct voltage is preferable. Further, if the control unit for regulating the power source on the basis of the detected value of current passed through the electrode is used to regulate the power source in such a manner that the amount of charges suitably forming the first and second deposited metals is supplied from the power source, the preparation of the dielectric film sample for observation of defects can be automated, and supply of charge can be performed accurately.

FIG. 1 shows an embodiment of the detection processing apparatus for carrying out the above-described defect detection method. This detection processing apparatus 1 is constituted of the processing part 2 and the processing control part 3, and the processing part 2 is constituted of the storage vessel 4 for accommodating electrolyte solution E and two electrode parts 5*a*, 5*b* arranged in the storage vessel 4. The electrode part 5*a* is constituted of the electrode plate 7*a* which is contactingly fixed to sample 6 for applying voltage to sample 6 and the holding jig 8 for contactingly fixing the sample 6 to the electrode plate 7*a*.

The holding jig 8 is made of an acid-resistant resin such as polytetrafluoroethylene, etc. In this embodiment, the electrode part 5*b* is composed of an electrode plate 7*b*. The processing control part 3 is constituted of a variable direct current voltage generator 9 capable of supplying direct voltage in a variable direction at a valuable level, an ammeter 10, a voltmeter 11 and an arithmetic processing unit 12. The variable direct voltage generator 9 is electrically connected to the electrode plate 7*a* in the electrode part 5*a* and to the electrode plate 7*b*, and the electrical connection between the variable direct current voltage generator 9 and the electrode plate 7*a* is formed via ammeter 10 and the holding jig 8. The sample 6 in this embodiment is a silicon substrate 13' of constant thickness having a dielectric film (SiO$_2$ film) 13 of a predetermined thickness, and the surface of the dielectric film 13 is arranged in parallel with the electrode plate 7*b*. The surface of the electrode plate 7*a* is provided with sharp and fine uneven portions penetrating through a natural oxide film on the back face of the silicon substrate 13' into the inside silicon to electrically connect to the sample 6. Although not shown in FIG. 1, a fixing stand for fixing the holding jig 8 itself and an electrode holding jig for fixing the electrode part 5*b*, a magnetic stirrer for making the concentration of the electrolyte solution E always uniform and a resistor for minimizing a fluctuation in applied direct current voltage can be provided as necessity arises.

In the above construction, when voltage is applied with the electrode plate 7*a* as a cathode and the electrode plate 7*b* as an anode, the same voltage is applied to the dielectric film 13 by the electrode plate 7*a*. Depending on the presence or absence of defect 14, a difference in current values occurs locally on the surface of the dielectric film 13, and the metal component in the electrolyte solution E is initiated to be deposited on the surface of the dielectric film 13 at the central position corresponding to defect 13, thus forming a spot of the deposited metal 15 at that position.

The current value measured with ammeter 10 is sent to the arithmetic processing unit 12, and on the basis of this value, the time of applying normal current is calculated from the total charges necessary for forming the first deposited metal. Alternatively, the voltage in the variable direct current voltage generator 9 is controlled so as to apply the total charges necessary for a predetermined application time. After the current application time is elapsed, the arithmetic processing unit 12 switches the variable direct voltage generator 9 to flow reverse current to the electrode plates 7*a*, 7*b*. Further, the time of applying reverse current or suitable voltage is calculated from the total charges of reverse current necessary for predetermined elution of the metal on the basis of the current value determined in ammeter 10, and the variable direct current voltage generator 9 is controlled. Further, the second deposited metal is formed by switching to normal current.

The detection processing apparatus 1 also comprises an additive container 16 having a nozzle with a control valve 17 for supplying an additive liquid. The control valve 17 is possibly controlled by the control unit 12. The additive container 16 reserves, as the additive liquid, an aqueous solution dissolving a metal which is different from the metal contained in the electrolyte solution E. If the control valve is opened, the metal composition of the electrolyte solution E is changed by supply of the additive liquid. Moreover, the storage vessel 4 has a drain pipe with a control valve 18. If another type of electrolyte solution is charged into the additive container 16, and if it is supplied into the storage vessel 4 while the controle valve 18 is opened, the electrolyte solution E in the storage vessel 4 is replaced with it.

The sample 6 having the metal deposited at the position corresponding to defect 14 by the detection processing apparatus 1 in FIG. 1 can be observed by using physical observation means such as optical microscope, scanning electron microscope etc. Accordingly, such an observation means is arranged adjacent to the detection processing apparatus.

Figure 2A:
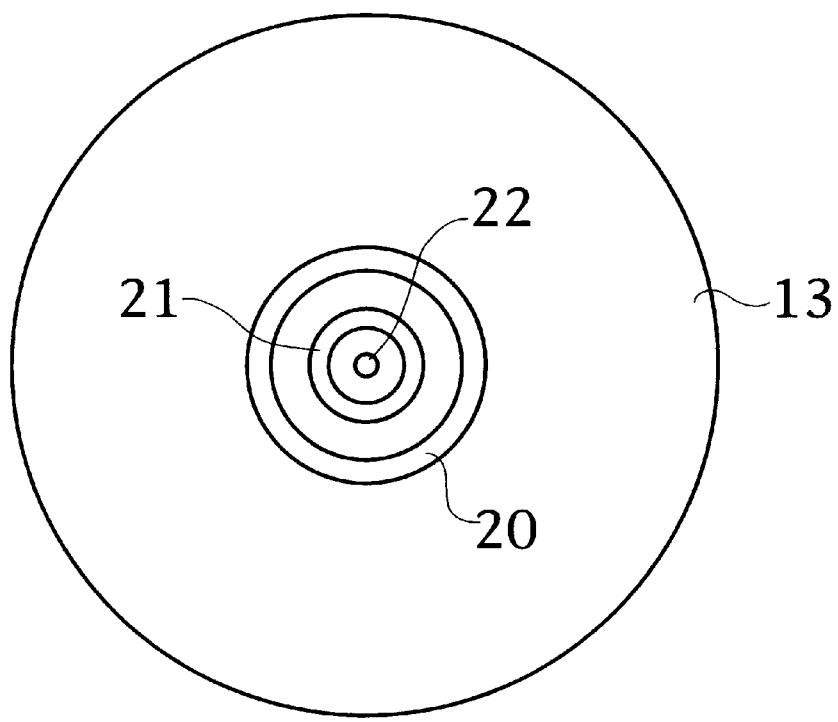
FIG. 2A is a plan view of a substrate for explaining one embodiment of the method of detecting defects according to the present invention.
Figure 2B:
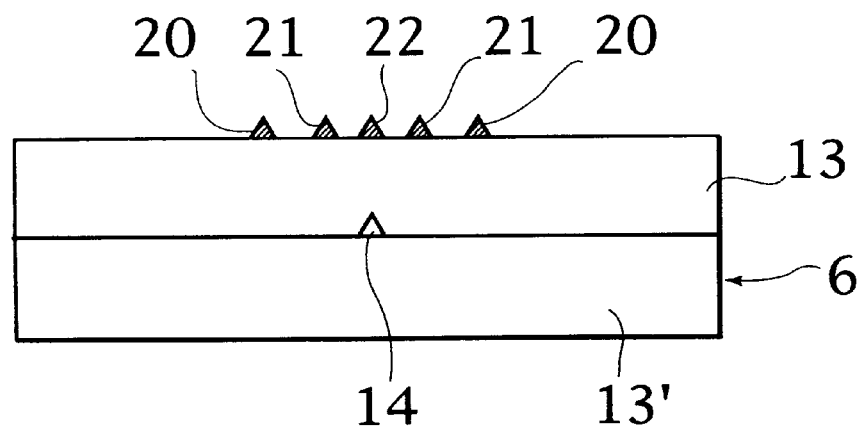
FIG. 2B is a sectional view of the substrate.

Hereinafter, an example of detection process using the above detection processing apparatus 1 is illustrated by reference to FIG. 2A, 2B.

The electrolyte solution E containing copper ions is accommodated in the storage vessel 4 in the detection processing apparatus 1, and voltage is applied across the electrode plate 7a as a cathode and the electrode plate 7b as an anode whereby copper is deposited on the surface position corresponding to defect 14 in the dielectric film 13 of the sample 6. Then, when applied voltage is lowered while reverse voltage, i.e. voltage in the reverse direction, is applied to the electrode plate 7a as an anode and the electrode plate 7b as a cathode, the copper is initiated to be eluted from the center of the deposited copper, and as shown in FIG. 2A, the annular deposited copper 20 is obtained on the dielectric film 13. Thereafter, applied voltage is further lowered and normal voltage is applied to the electrode plate 7a as a cathode and the electrode plate 7b as an anode, copper is deposited again as a concentric circle in the center of the annular deposited copper 20. When applied voltage is further lowered and reverse voltage is applied to the electrode plate 7a as an anode and the electrode plate 7b as a cathode, copper is initiated to be eluted from the central part of the inside deposited copper, and double annular copper deposits 20, 21 are obtained. Thereafter, a solution containing other metal ions is added to the electrolyte solution from the additive container 16, and when applied voltage is further lowered and normal voltage is applied to the electrode plate 7a as a cathode and the electrode plate 7b as an anode, the other metal 22 is deposited as a concentric circle in the center of annular copper deposits 20, 21. The deposited metal 22 also contains copper depending on the state of the electrolyte solution E.

The method of detecting defects according to the present invention can be applied not only to a single dielectric film but also to dielectric film formed on the surface of an electrically conductive base such as metal substrate or on the surface of semiconductor substrate. Further, the present method can be applied to detection of defects in various dielectric film such as silicon dioxide, silicon nitride or other metal oxides, nitrides, carbides, etc. If a thick conductive film is present on the surface of the dielectric film, the conductive film prevents precise electrodeposition, thus making detection of defects impossible, but in the case of a very thin conductive film, detection is feasible because its effect is not very high and negligible. Accordingly, the method of detecting defects according to the present invention can also be applied to cases where a thin film of electrically conductive material such as polysilicon is present on the dielectric film.

EXAMPLE

Hereinafter, the embodiment of the present invention is described in detail by reference to experimental results.

Example 1

A boron dope Si wafer of 150 mm (6 inches) in diameter (specific resistance: 6.9 Ωcm, thickness: 625 µm) was provided thereon by the thermal oxidation method with silicon nitride film of 200 Å thickness as dielectric film. The following procedures were conducted by using this sample substrate as the sample 6.

(Procedure 1)

About 2 N nitric acid and about 2 N hydrochloric acid were mixed at a ratio of 1:1 (ratio by volume) to prepare a mixed acid solution. The above sample 6 was washed with this mixed acid solution at about 25° C. for 10 minutes, then washed with pure water, and dried.

The opposite face (back) of the dried sample 6 to the dielectric film 13 was pressingly contacted to the electrode plate 7a as shown in FIG. 1 and fixed to the holding jig 8 in the detection processing apparatus 1 such that the backs of the electrode plate 7a and of the sample 6 were shielded from the surroundings and arranged in the storage vessel 4 as shown in FIG. 1. The details of each constitutional part of the detection processing apparatus 1 are as follows:

(Storage vessel 4) A top-open rectangular vessel of 25 cm length×15 cm width×25 cm height made of transparent polyvinyl chloride of 0.4 cm in thickness.

(Electrode plate 7a) A flat copper plate of 150 mmφ (6 inches) diameter×0.1 cm thickness having uneven portions of 1 to 20 µm in depth made by scratching its whole surface with a pair of stainless steel tweezers.

(Electrode plate 7b) A flat copper plate of 15 cm length× 15 cm width×0.05 cm thickness.

(Holding jig 8) A polytetrafluoroethylene vessel of 200 mmφ diameter×2.3 cm thickness. Two rubber O-shaped rings, the Teflon vessel and an acrylic screw were used for fixing the sample 6.

Copper chloride was dissolved in an aqueous solution of hydrochloric acid to prepare about 0.1 N hydrochloric acid solution containing copper at a concentration of about 0.001 mol/L as an electrolyte solution. This electrolyte solution was introduced into the storage vessel 4. Only the surface of the silicon dioxide film 13 in the sample 6 was thus contacted with the electrolyte solution.

A voltage of +10 V (the potential of the electrode plate 7b minus the potential of the electrode plate 7a) was applied for 20 minutes to the electrode plate 7a and electrode plate 7b [first step], during which the average current value was +0.80 µA. Copper was thereby deposited on the surface of the dielectric film 13 in the sample 6.

Thereafter, the variable direct voltage generator 9 was switched to apply a voltage of −9 V (average current value: −0.72 µA) for 18 minutes [second step], a voltage of +5 V (average current value: +0.40 µA) for 5 minutes [third step], a voltage of −4.5 V (average current value: −0.36 µA) for 4.5 minutes [fourth step] and a voltage of +2 V (average current value: +0.16 µA) for 1 minute [fifth step].

Thereafter, the sample 6 was washed with pure water and then dried, and the surface of the dielectric film 13 on the sample 6 was observed by using optical microscope and scanning electron microscope. As a result of the microscopic observation, it was found that deposited copper consisting of two concentric annular copper deposits around the position corresponding to defects on the dielectric film and a circular deposit inside the concentric annular deposits was formed. The outermost diameter of the copper deposit was in the range of 0.1 to 30 µm, and even for a copper deposit of an outermost diameter of 10 µm or more, the central position of the defect could be specified with accuracy within the maximum error of 0.1 µm.

(Procedure 2)

An electrolyte solution containing copper was prepared in the same manner as in Procedure 1 and divided into two portions, and one portion was used as the first electrolyte solution. Separately, gold was dissolved in aqua regia and hydrochloric acid was added to it to prepare gold solution in hydrochloric acid, which was added to the other electrolyte solution to prepare an about 0.1 N hydrochloric acid solution containing copper at a concentration of about 0.001 mol/L and gold at a concentration of about 0.00003 mol/L and used as the second electrolyte solution.

The same procedure as in Procedure 1 was carried out except that the first electrolyte solution was used in the first to fourth steps in Procedure 1, and the second electrolyte solution was used in the fifth step, and then the surface of the dielectric film 13 in the sample 6 was observed by using an optical microscope and scanning electron microscope. The current values passed in the first to fifth steps are as shown in Table 1.

As a result of the microscopic observation, it was found that deposits consisting of two concentric annular deposits around the position corresponding to a defect on the dielectric film 13 and their inside circular deposit were formed. The central circular deposit contained gold and the surrounding annular deposits were made of copper. The outermost diameter of the deposit was in the range of 0.1 to 30 μm, and even for a copper deposit of an outermost diameter of 10 μm or more, the central position of the defect could be specified with accuracy within the maximum error of 0.1 μm.

(Procedure 3)

The same procedure as in Procedure 1 was carried out except that the voltage application in the second to fifth steps in Procedure 1 was omitted, and then the surface of the dielectric film 13 on the sample 6 was observed by using optical microscope and scanning electron microscope. The current value passed in the first step is as shown in Table 1.

As a result of the microscopic observation, it was found that a circular copper deposit was formed around the position corresponding to a defect on the dielectric film 13. The outermost diameter of the deposit was in the range of 0.1 to 30 μm, and for a copper deposit with a diameter of 10 μm or more, the central position of the defect was difficult to specify with accuracy in the maximum error of 5 μm.

Example 2

A phosphorus dope Si wafer of 150 mm diameter (6 inches) (specific resistance: 3.7 Ωcm, thickness: 625 μm) was provided thereon by the CVD method with silicon nitride film of 300 Å thickness as dielectric film. The following procedures were conducted using this sample substrate as the sample 6.

(Procedure 4)

About 2 N nitric acid and about 2 N hydrochloric acid were mixed at a ratio of 1:1 (ratio by volume) to prepare a mixed acid solution. The above sample 6 was washed with this mixed acid solution at about 25° C. for 10 minutes, then washed with pure water, and dried.

The opposite face (back) of the dried sample 6 to the dielectric film 13 was pressingly contacted to the electrode plate 7a as shown in FIG. 1 and fixed to the holding jig 8 in the detection processing apparatus 1 such that the backs of the electrode plate 7a and of the sample 6 were shielded from the surroundings and arranged in the storage vessel 4 as shown in FIG. 1. The details of each constitutional part of the detection processing apparatus 1 are the same as in Example 1.

Copper chloride was dissolved in an aqueous solution of hydrochloric acid to prepare about 0.1 N hydrochloric acid solution containing copper at concentration of about 0.001 mol/L as an electrolyte solution. This electrolyte solution was introduced into the storage vessel 4. Only the surface of the silicon nitride film 13 on the sample 6 was thus contacted with the electrolyte solution.

A voltage of +11 V (the potential of the electrode plate 7b minus the potential of the electrode plate 7a) was applied for 20 minutes to the electrode plate 7a and electrode plate 7b [first step], during which the average current value was +0.87 μA. Copper was thereby deposited on the surface of the dielectric film in the sample 6.

Thereafter, the variable direct voltage generator 9 was switched to apply a voltage of −10 V (average current value: −0.71 μA) for 18 minutes [second step], a voltage of +5 V (average current value: +0.39 μA) for 5 minutes [third step], a voltage of −4.5 V (average current value: −0.34 μA) for 4.5 minutes [fourth step] and a voltage of +2 V (average current value: +0.15 μA) for 1 minute [fifth step].

Thereafter, the sample 6 was washed with pure water and then dried, and the surface of the dielectric film 13 in the sample 6 was observed by using optical microscope and scanning electron microscope. As a result of the microscopic observation, it was found that deposited copper consisting of two concentric annular copper deposits around the position corresponding to defects on the dielectric film and their inside circular deposit was formed. The outermost diameter of the copper deposit was in the range of 0.1 to 30 μm, and even for a copper deposit of an outermost diameter of 10 μm or more, the central position of the defect could be specified with accuracy within the maximum error of 0.1 μm.

(Procedure 5)

An electrolyte solution containing copper was prepared in the same manner as in Procedure 4 and divided into two portions, and one portion was used as the first electrolyte solution. Separately, platinum was dissolved in aqua regia and hydrochloric acid was added to it to prepare platinum solution in hydrochloric acid, which was added to the other electrolyte solution to prepare about 0.1 N hydrochloric acid solution containing copper at concentration of about 0.001 mol/L and platinum at concentration of about 0.00003 mol/L and used as the second electrolyte solution.

The same procedure as in Procedure 4 was repeated except that the first electrolyte solution was used in the first to fourth steps in Procedure 4, and the second electrolyte solution was used in the fifth step, and then the surface of the dielectric film 13 in the sample 6 was observed by using an optical microscope and scanning electron microscope. The current values flowed in the first to fifth steps are as shown in Table 1.

As a result of the microscopic observation, it was found that deposits consisting of two concentric annular deposits around the position corresponding to a defect on the dielectric film 13 and their inside circular deposit were formed. The central circular deposit contained platinum and the surrounding annular deposits were made of copper. The outermost diameter of the deposit was in the range of 0.1 to 30 μm, and even for a copper deposit of an outermost diameter of 10 μm or more, the central position of the defect could be specified with accuracy within the maximum error of 0.1 μm.

(Procedure 6)

The same procedure as in Procedure 4 was repeated except that the voltage application in the second to fifth steps in Procedure 4 was omitted, and then the surface of the dielectric film 13 in the sample 6 was observed by using an optical microscope and scanning electron microscope. The current value passed in the first step is as shown in Table 1.

As a result of the microscopic observation, it was found that a circular copper deposit was formed around the position corresponding to a defect on the dielectric film 13. The outermost diameter of the deposit was in the range of 0.1 to 30 μm, and for a copper deposit of an outermost diameter of 10 μm or more, the central position of the defect was difficult to specify with accuracy in the maximum error of 5 μm.

Example 3

A phosphorus dope Si wafer of 150 mm diameter (6 inches) (specific resistance: 3.0 Ωcm, thickness: 625 μm) was provided by the CVD method with silicon dioxide film of 250 Å thickness as dielectric film and further thereon by the CVD method with polysilicon film of 20 nm thickness. The following procedures were conducted by using this sample substrate as the sample 6.
(Procedure 7)

About 2 N nitric acid and about 2 N hydrochloric acid were mixed at a ratio of 1:1 (ratio by volume) to prepare a mixed acid solution. The above sample was washed with this mixed acid solution at about 25° C. for 10 minutes, then washed with pure water, and dried.

The opposite face (back) of the dried sample 6 to the dielectric film 13 was pressingly contacted to the electrode plate 7a as shown in FIG. 1 and fixed to the holding jig 8 in the detection processing apparatus 1 such that the backs of the electrode plate 7a and of the sample 6 were shielded from the surroundings and arranged in the storage vessel 4 as shown in FIG. 1. The details of each constitutional part of the detection processing apparatus 1 are the same as in Example 1.

Copper chloride was dissolved in an aqueous solution of hydrochloric acid to prepare about 0.1 N hydrochloric acid solution containing copper at concentration of about 0.001 mol/L as an electrolyte solution. This electrolyte solution was introduced into the storage vessel 4. Only the surface of the polysilicon film in the sample 6 was thus contacted with the electrolyte solution.

A voltage of +11 V (the potential of the electrode plate 7b minus the potential of the electrode plate 7a) was applied for 20 minutes to the electrode plate 7a and electrode plate 7b [first step], during which the average current value was +0.79 μA. Copper was thereby deposited on the surface of polysilicon film.

Thereafter, the variable direct voltage generator 9 was switched to apply a voltage of −9 V (average current value: −0.65 μA) for 18 minutes [second step], a voltage of +5 V (average current value: +0.36 μA) for 5 minutes [third step], a voltage of −4.5 V (average current value: −0.32 μA) for 4.5 minutes [fourth step] and a voltage of +2 V (average current value: +0.14 μA) for 1 minute [fifth step].

Thereafter, the sample 6 was washed with pure water and then dried, and the surface of the polysilicon film on the sample 6 was observed by using an optical microscope and scanning electron microscope. As a result of the microscopic observation, it was found that deposited copper consisting of two concentric annular deposits around the position corresponding to defects on the dielectric film and their inside circular deposit was formed. The outermost diameter of the copper deposit was in the range of 0.1 to 30 μm, and even for a copper deposit of an outermost diameter of 10 μm or more, the central position of the defect could be specified with accuracy within the maximum error of 0.1 μm.
(Procedure 8)

An electrolyte solution containing copper was prepared in the same manner as in Procedure 7 and divided into two portions, and one portion was used as the first electrolyte solution. Separately, gold was dissolved in aqua regia and hydrochloric acid was to it to prepare gold solution in hydrochloric acid, which was added to the other electrolyte solution to prepare about 0.1 N hydrochloric acid solution containing copper at concentration of about 0.001 mol/L and gold at concentration of about 0.00003 mol/L and used as the second electrolyte solution.

The same procedure as in Procedure 7 was carried out except that the first electrolyte solution was used in the first to fourth steps in Procedure 4, and the second electrolyte solution was used in the fifth step, and then the surface of the polysilicon film in the sample 6 was observed by using an optical microscope and scanning electron microscope. The current values passed in the first to fifth steps are as shown in Table 1.

As a result of the microscopic observation, it was found that deposits consisting of two concentric annular deposits around the position corresponding to a defect on the polysilicon film and their inside circular deposit were formed. The central circular deposit contained gold and surrounding annular deposits were made of copper. The outermost diameter of the deposit was in the range of 0.1 to 30 μm, and even for a copper deposit of an outermost diameter of 10 μm or more, the central position of the defect could be specified with accuracy within the maximum error of 0.1 μm.
(Procedure 9)

The same procedure as in Procedure 7 was repeated except that the voltage application in the second to fifth steps in Procedure 7 was omitted, and then the surface of the polysilicon film in the sample 6 was observed by using optical microscope and scanning electron microscope. The current value passed in the first step is as shown in Table 1.

As a result of the microscopic observation, it was found that a circular copper deposit was formed around the position corresponding to a defect in the polysilicon film.

The diameter of the deposit was in the range of 0.1 to 30 μm, and for a large deposit with a diameter of 10 μm or more, the central position of the defect was difficult to specify with accuracy in the maximum error of 5 μm.

TABLE 1

| | Average Current Value (μA) | | | | |
|---|---|---|---|---|---|
| Procedure | 1st step | 2nd step | 3rd step | 4th step | 5th step |
| 1 | +0.80 | −0.72 | +0.40 | −0.36 | +0.16 |
| 2 | +0.80 | −0.72 | +0.40 | −0.36 | +0.16 |
| 3 | +0.80 | | | | |
| 4 | +0.87 | −0.71 | +0.39 | −0.34 | +0.15 |
| 5 | +0.87 | −0.71 | +0.39 | −0.34 | +0.15 |
| 6 | +0.87 | | | | |
| 7 | +0.79 | −0.65 | +0.36 | −0.32 | +0.14 |
| 8 | +0.79 | −0.65 | +0.36 | −0.32 | +0.14 |
| 9 | +0.79 | | | | |

As is evident from the foregoing, the presence of a defect in dielectric film can be easily recognized and simultaneously the central position of the defect can be highly accurately specified by forming the first annular deposited metal encompassing the surface position corresponding to the position of the defect in the dielectric film and the second deposited metal located in said surface position. Furthermore, a sample for observing defects can be easily and rapidly prepared.

In addition, a noble metal is deposited as the second metal by adding the noble metal to an electrolyte solution used in the step of depositing the second deposited metal, so that the surface position corresponding to the central position of the defect can be rapidly specified and this is also advantageous in visual observation.

It must be understood that the invention is in no way limited to the above embodiments and that many changes may be brought about therein without departing from the scope of the invention as defined by the appended claims.

What is claimed is:

1. A method of detecting a defect in a dielectric film by electrifying the dielectric film, with application of voltage, in an electrolyte solution containing a metal in such a manner that the dielectric film is charged negatively, whereby the metal is deposited on the dielectric film at a position corresponding to the defect, comprising:

a first deposition step for forming a first metal deposit on the dielectric film in an annular form surrounding the position corresponding to the defect; and a second deposition step for forming a second metal deposit located on the position corresponding to the defect, on the dielectric film.

2. The detecting method of claim 1, wherein the second metal deposit has a dimension which is smaller than an inner bore of the first metal deposit.

3. The detecting method of claim 1, wherein the first deposition step comprises:

an electrodepositing step for electrifying the dielectric film such as to charge the dielectric film negative and to form a circular metal deposit having a dimension corresponding to an outer diameter of the first metal deposit; and an eluation step for electrifying the dielectric film such as to charge the dielectric film positive and to elute a central portion of the circular metal deposit on the position corresponding to the defect, the central portion having a dimension which is substantially the same as an inner diameter of the first metal deposit, thereby the circular metal deposit is changed into the annular form of the first metal deposit.

4. The detecting method of claim 3, wherein the electric charge amount, Ed, which is supplied to the dielectric film by electrification at the electrodepositing step, the electric charge amount, Es, which is supplied to the dielectric film by electrification at the eluation step, and the electric charge amount, Ec, which is supplied to the dielectric film by electrification at the second metal deposition step are in a relationship which is represented by the formula:

$$|Ed|>|Es|>|Ec|.$$

5. The detecting method of claim 3, wherein each of the electric charge amounts, Ed, Es and Ec, are regulated by controlling voltage applied to the dielectric film at each of the electrodepositing step, the eluation step and the second metal deposition step.

6. The detecting method of claim 1, wherein the first metal deposit formed at the first deposition step comprises an N number (N is a natural number) of annular deposits being concentrically formed with each other and having different dimensions respectively.

7. The detecting method of claim 1, wherein the first metal deposition step comprises an N number of cycles of operation, wherein the Mth (M=1,2, . . . N) cycle of operation comprises:

an electrodepositing step for electrifying the dielectric film such as to charge the dielectric film negative and to form a Mth circular deposit having a dimension corresponding to an outer diameter of the Mth annular deposit; and an eluation step for electrifying the dielectric film such as to charge the dielectric film positive and to elute a central portion of the Mth circular deposit on the position corresponding to the defect, the central portion having the same dimension as an inner diameter of the Mth annular deposit, thereby the Mth circular deposit is changed into the Mth annular deposit.

8. The detecting method of claim 7, wherein an amount of the electric charge supplied to the dielectric film by electrification at the Mth electrodepositing step is represented by $Ed_M$ (M=1,2, . . . N), an amount of the electric charge supplied to the dielectric film by electrification at the Mth eluation step is represented by $ES_M$ (M=1,2, . . . N), and an amount of the electric charge supplied to the dielectric film by electrification at the second metal deposition step is represented by Ec, and wherein the amounts, $Ed_M$, $Es_M$ and Ec, are in a relationship which is represented by the formula:

$$|Ed_1|>|Es_1|>|Ed_2|>|Es_2| \ldots >|Ed_N|>|Es_N|>|Ec|.$$

9. The detecting method of claim 1, further comprises:

a changing step for changing the metal composition of the electrolyte solution so that the first deposition step is performed in a electrolyte solution having a first metal composition and the second deposition step is performed in a electrolyte solution having a second metal composition which is different from the first metal composition.

10. The detecting method of claim 9, wherein the changing step comprises:

adding a metal solution into the electrolyte solution after the first deposition step so that the metal composition of the electrolyte solution is changed from the first metal composition to the second metal composition.

* * * * *

UNITED STATES PATENT AND TRADEMARK OFFICE
CERTIFICATE OF CORRECTION

PATENT NO. : 6,118,280
DATED : September 12, 2000
INVENTOR(S) : Hideki Matsunaga et al It is certified that error appears in the above-identified patent and that said Letters Patent is hereby corrected as shown below:

Title Page,
Item [57] in the Abstract,
Line 14, "controlably" should read -- controllably --.

Column 18, claim 9,
Line 39, " a electrolyte" should read -- an electrolyte.
Line 41, a electrolyte" should read-- electrolyte --.

Signed and Sealed this

Twenty-eighth Day of August, 2001

Attest:

*Attesting Officer*

NICHOLAS P. GODICI
*Acting Director of the United States Patent and Trademark Office*